United States Patent [19]

Türk et al.

[11] 4,001,379
[45] Jan. 4, 1977

[54] PROCESS OF MAKING SUPERFINE AMORPHOUS HIGH STRUCTURAL SILICIC ACID

[75] Inventors: Günter Türk, Gross-Auheim; Joseph Welsch, Neu-Isenburgh, both of Germany

[73] Assignee: Deutsche Gold-und Silber-Scheideanstalt vormals Roessler, Germany

[22] Filed: Sept. 21, 1972

[21] Appl. No.: 290,884

Related U.S. Application Data

[63] Continuation of Ser. No. 199,054, Nov. 15, 1971, abandoned, which is a continuation of Ser. No. 849,739, April 28, 1969, abandoned.

[30] Foreign Application Priority Data

Apr. 27, 1968 Germany .......................... 1767332

[52] U.S. Cl. .............................. 423/339; 423/355; 106/288 B; 260/29.1 R; 426/97; 424/357 GP
[51] Int. Cl.² ................... C01B 33/18; C01B 33/12
[58] Field of Search .................. 423/339, 659, 335; 106/288 B

[56] References Cited

UNITED STATES PATENTS

| | | | |
|---|---|---|---|
| 2,588,853 | 3/1952 | Kumins et al. ...................... | 423/339 |
| 2,940,830 | 6/1960 | Thornhill ............................ | 423/339 |
| 2,973,246 | 2/1961 | Harman et al. ..................... | 423/335 |
| 3,041,140 | 6/1962 | Alexander .......................... | 423/335 |
| 3,227,607 | 1/1966 | Mays et al. ...................... | 106/288 B |
| 3,235,331 | 2/1966 | Nauroth et al. ................... | 423/339 |
| 3,337,299 | 8/1967 | Burke, Jr. ........................... | 423/332 |
| 3,367,742 | 2/1968 | Marotta et al. ..................... | 423/335 |
| 3,372,046 | 3/1968 | Burke, Jr. ........................ | 106/288 B |
| 3,386,810 | 6/1968 | Burke, Jr. et al. ................... | 23/285 |
| 3,403,109 | 9/1968 | Colgan ............................. | 252/451 |
| 3,826,814 | 7/1974 | Illigen et al. ....................... | 423/335 |

FOREIGN PATENTS OR APPLICATIONS 818,095   8/1959   United Kingdom ............... 423/338

OTHER PUBLICATIONS

German Patents Abstracts, 1964, vol. 4, No. 22, (Apr. 30, 1964), Plastics, Metal Finishing, p. 1, Derwent Publications, Ltd., London.
John H. Perry's "Chemical Engineers Handbook," 4th Ed., 1963, Chapter 8, p. 41, McGraw-Hill Book Co., Inc., New York City, N.Y.

*Primary Examiner*—Edward Stern
*Attorney, Agent, or Firm*—Cushman, Darby & Cushman

[57] ABSTRACT

Superfine amorphous, high structure silicic acid is made by subjecting the components in the precipitation reaction, that is, an acid or acidic substance and an alkali-metal silicate solution to a shearing force during the alkaline phase of the precipitation reaction, the shearing force being applied by passing the reaction mass in a continuous flow through a dispersing device and the dispersing device being operated with an hourly throughput frequency of at least $10h^{-1}$, the said frequency being determined as the ratio of the performance of the dispersing device to the initial volume of the reaction mass.

The high structure silicic acid is particularly useful as carrier and filler for pesticides, animal feed additives and as matting agent for lacquers.

9 Claims, 3 Drawing Figures

PROCESS OF MAKING SUPERFINE AMORPHOUS HIGH STRUCTURAL SILICIC ACID

CROSS-REFERENCE TO RELATED APPLICATIONS

This application is a continuation of our prior application Ser. No. 199,054, filed Nov. 15, 1971, which is in turn a continuation of our application Ser. No. 849,739, filed Apr. 28, 1969, both of which are now abandoned.

BACKGROUND OF THE INVENTION

The invention relates to a process of making superfine amorphous silicic acid by reacting alkali-metal silicate solutions with an acid or an acidic substance and, if desired, in the presence of neutral salts. These silicic acids are distinguished by a very fine grain size, high structure and very good dispersing properties in water and organic media.

Specific types of silicic acids are known which have a structure different from that of normal silicic acids. There are wet-precipitated silicic acids or silica gels which form high structure products by virtue of specific modifications of the drying process. These products include aerogels, silica gels or silicic acids in which the intermicellar liquid prior to drying consists of organic solvents or mixtures of such solvents with water. In this group belong also spray-dried silicic acids and silica gels.

Aerogels have previously been obtained by drying of so-called organogels under critical conditions. This process is very expensive because of the necessity to use large amounts of relatively expensive organic solvents and the employment of autoclaves which are discontinuously operated at extreme drying temperatures (high pressures and high temperatures). The aerogels have therefore as a rule been used only for special purposes.

It is also known to replace the intermicellar liquid (water) in normal hydrogels or silicic acids partly or entirely by corresponding organic solvents. Through the stage of organogels or organosilicic acids there are thus likewise obtained $SiO_2$-containing materials with an increased structure at normal drying conditions. This process, similar to the one for making aerogels, also requires the use of more expensive organic solvents.

More recently, the use of spray-dried silicic acid has become accepted for certain applications. These types of silicic acids are likewise distinguished by a higher structure, though this structure is not comparable with that of the types previously discussed. The spray-drying, apart from the requirement of rather expensive appliances, is not possible without an increased use of energy input. The products made by this process therefore can likewise be used only for special purposes.

From German patent No. 1,000,793 a process is known whereby alkali-metal silicate solutions are reacted with acids or acidic-acting substances, if desired in the presence of neutral salts. This process results in well-dispersible finely divided silicic acid if the precipitation of the silicic acid is effected by a rapid and intensive mixing of the reaction component by application of a high shearing force based on a steep speed gradient. This high speed gradient in these cases is produced by a colloid mill.

In this patent, it has also been proposed to carry out the precipitation step in two tanks or vessels of different size. The alkali-metal silicate solution is initially disposed in the larger tank and is continuously pumped throughout the entire precipitation step up to its completion through the smaller vessel. The result is the mixing of the alkali-metal silicate solution with the acid in the smaller precipitation vessel which latter must have a volume relative to the total volume of the reaction solution amounting to a specific value, that is, between 1:2 and 1:100 and preferably between 1:4 and 1:20. The difference in the alkali-metal content of the portion of the reaction mass which is discharged from the precipitation tank and the fraction which at the same time enters the precipitation tank should always be less than 10% and preferably less than 3% relative to the alkali-metal contents of the initial alkali-metal silicate solution.

The silicic acids made by this process are distinguished by a higher structure compared with conventionally made precipitated silicic acids and are particularly useful as reinforcing fillers in synthetic rubbers. However, this process is likewise rather costly and cumbersome because of the use of precipitation tanks of different sizes and because of the long periods necessary for the dispersion and the thus required high energy input.

The discussion so far makes it quite apparent that the making of high structure silicic acids either requires special drying methods or expensive precipitation apparatus. The thus-obtained products can therefore be used only for special applications.

Since all these silicic acids types have a structure different from the products obtained in conventional precipitation processes, it is desirable to determine the presence and size of structure by accurate measurements. In the following the concept of the so-called structure and the methods for determining it by accurate measurements shall therefore be discussed.

Structure of a silic acid is meant to refer to the size of the cavities or three-dimensional measurements which arise from the loose aggregation of primary particles to form more-or-less stable secondary particles or aggregates. These cavities, though in form of capillaries, do not have measurements as strictly defined as the cavities in, for instance, a porous body. The size of the so-called intergranular volume of the secondary particles of silicic acid permits, however, to draw conclusions regarding the packing density of the primary particles, and thus regarding the structure of the silicic acid.

In order to determine the capillary volume of a silicic acid, it is possible to use the absorption of a more-or-less defined absorption liquid as physical measuring standard.

In case of the structure of silicic acids, it is possible to arrive at a measurement of the oil absorption by means of the so-called Brabender-Cabot method a) V. A. Sljaka et al, Cabot-release for ASTM D-24-Meeting 1-5-63 and b) E. R. Eaton, J. S. Middleton (Cabot Corp.) Rubber World, 152, 94-100 (1965).

Figure 1:
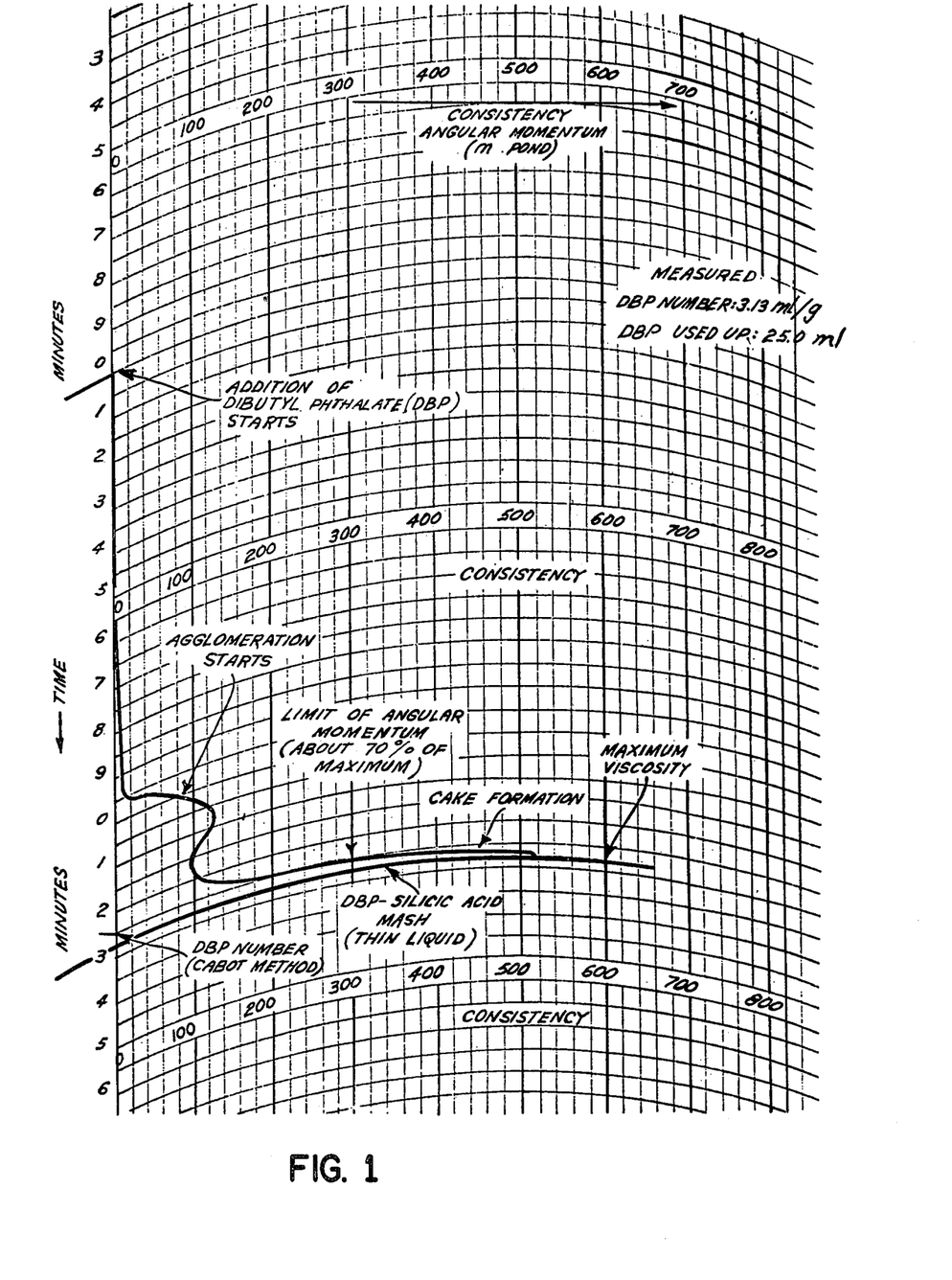
FIG. 1 (already discussed in connection with the background of the invention) shows a viscosity-time diagram of a high structure silicic acid.

FIG. 1, which will be identified further below, illustrates the plastogram of a high structure silicic acid. The consistency of the oil-silicic acid mixture, measured in units of angular momentum, is recorded as a function of the time (in minutes) or as a function of the added amount of oil. From the diagram of FIG. 1 it is thus possible to readily determine the viscosity maximum and the amount of oil which was added up to the point where specific landmark points were reached on the viscosity curve. This amount of oil is stated as specific oil number in ml oil per gram.

The measurements were carried out with the Brabender-Cabot absorptometer which was developed by the Cabot Company of the United States in collaboration with the W. C. Brabender Instrument Company. This apparatus is particularly equipped for oil absorption investigations in carbon blacks and fillers and is provided with a special Cabot kneader. The Cabot kneader is connected with a Brabender plastograph. Its kneading chamber is open at the top and is covered by a plate which prevents the entry of dust into the silicic acid powder in the initial phase. After adding oil in a continuous flow to the kneader there is reached a point where the oil-silic acid mixture starts to agglomerate whereupon the angular momentum rises first slowly and then very steeply. This agglomeration is followed by cake formation (see FIG. 1). The cakes are fragments of the total mass which are in a pulpy consistency and are escaping the mixing action because of the open kneading chamber and thus subsequently start dancing on the kneader paddles. Oil that is then added does wet these cakes at their surface; it can, however, no longer be admixed homogeneously.

This process becomes apparent in the viscosity curve of the oil-silicic acid mixture (see FIG. 1), which shows that the curve outline, after initial slow rising, advances steeply towards a maximum and subsequently, while strongly oscillating around a mean value of the angular momentum (effect of the cake formation), will then decrease again upon further addition of oil. If the curve structure up to the agglomeration and the steep rise of the angular momentum is well reproducible for comparative tests, this is not true regarding the maximum value which depends on the cake formation and therefore relative to the added amount of oil is subject to slight changes (see J. Behre, G. Schramm in Gummi, Asbest, Kunststoffe 19, 912–922 (1966)).

The proposed ASTM norm avoids the possible measurement errors by adding oil--not up to the maximum but--up to a preceding more-or-less arbitrary limit value of the angular momentum, for instance a value of 70% of the maximum. This limit value which must be ascertained by tests for each type of silicic acid is therefore a condition of the reproducible determination of the oil absorption by filling materials.

The oil absorption value according to the Cabot method is determined as the amount of oil in ml/g filler which must be added up to reaching the said limit value. Preferably, dibutylphthalate (DBP) is used as the absorption liquid. The oil absorption is therefore expressed as the DBP number.

This method permits to accurately determine the structure of a precipitated silicic acid and to make an appraisal of the possible uses of silicic acids made by different processes as depending on the structure of the acid.

Since for special applications, particularly in the areas of the pesticide and lacquer technologies, the requirements as to quality of the employed silicic acid are very high, it is one of the objects of the present invention to make silicic acids with a well-defined and reproducible high structure while avoiding the shortcomings of the previously described prior-art processes.

A still more specific object of the invention is a finely distributed high structure silicic acid in the range of from 1 to 15 microns having a high DBP or oil number which acid can be obtained by suitable precipitation conditions and optimum mechanical action on the $SiO_2$ suspension and a controlled modification of the secondary particle distribution.

It is thus an object also of the invention to reduce the relatively high energy requirement of the process disclosed in German patent No. 1,000,793, that is to limit the time of the dispersing action to a minimum and thus to improve the economies of the process.

SUMMARY OF THE INVENTION

These objects are met by a process wherein a mixture of an acid or acidic-acting substance is effected with an alkali-metal silicate solution and the two components are caused to react so as to precipitate the silicic acid and to form a suspension thereof and wherein during this process a shearing force is applied to the reaction mass, specifically during the alkaline phase of the precipitation reaction by passing the reaction mass in a continuous flow through a dispersing device and wherein the dispersing device is operated with an hourly throughput frequency from at least 10 $h^{-1}$ and the said frequency is determined as the ratio of the performance of the dispersing device expressed in $m^3/h$ to the initial volume of the reaction mass expressed in $m^3$.

The invention also embraces the use of the thus-made silicic acids as the carrier material in pesticide compositions, animal feeds and as matting agents for lacquers.

DESCRIPTION OF THE PREFERRED EMBODIMENTS

The dispersing device may be constituted by (a) a flow-through dispersing device (dispersing pump), (b) a rotary pump, more specifically a centrifugal pump, or a side-channel pump or (c) a combination of a rotary pump and a flow-through dispersing device, constituting a high performance dispersing pump aggregate.

The precipitation may be effected in the presence of neutral salts.

Preferably the hourly frequency is between 20 and 100 $h^{-1}$ and the shearing force preferably is applied during the transition from the forming hydro-$SiO_2$-sol to the gradually flocculating silicic acid. A general range for the throughput frequence would be between about 10 and about 10,000 $h^{-1}$.

The terms hourly frequency and hourly throughput frequency refer to the ratio of hourly throughput of the dispersing device expressed in cubic meters per hour to the initial volume of the reaction mixture in cubic meters.

The alkali number during the precipitation should be between 10 and 40. The alkali number is equal to the titer value determined by the amount of n/10 HCl used up in forming 10 ml precipitation suspension. Preferably the alkali number is between 30 and 35.

Preferably the participants in the reaction are selected so as to obtain an $SiO_2$ end concentration above 65 g $SiO_2$/l and preferably between 80 and 100 g $SiO_2$/l.

These and further details of the reaction will now be discussed.

The dispersing device may be a dispersing pump through which the reaction medium passes in a continuous flow and which would require a higher input of about 0.30 kWh/kg $SiO_2$ whenever a high structure silicic acid additionally having a very fine grain size is wanted. On the other hand, if the silicic acid should have high structure but only a medium fine grain size, the use of a rotary pump operating with a specific dispersion force of 0.17 kWh/kg $SiO_2$ is sufficient.

Figure 3:
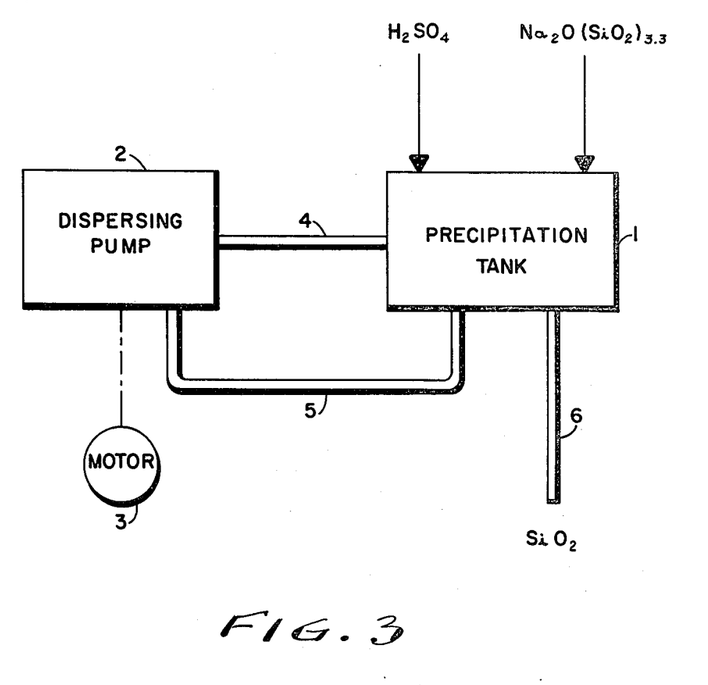
FIG. 3 is a diagrammatic view of a precipitation apparatus for use in the process of the invention.

An indication of the general type of apparatus used in the process of the invention will be found in FIG. 3. Reference numeral 1 refers to the precipitation tank, 2 is the dispersing pump, 3 the motor, 4 and 5 the ducts for the circulating mass, and 6 is the outlet.

It is a feature of the invention that by varying and combining different dispersing factors, such as, throughput frequency, timing and duration of the dispersion, it is possible to vary the structure or DBP number, the hardness of the granulate and therefore the range of the secondary grain of the silicic acid in a selective manner and within a definite range.

A further feature of the invention resides in the fact that by a controlled selection of the precipitation conditions and combination thereof with the optimum just-referred-to dispersion conditions it is possible to obtain an additional increase of the structure (DBP number).

For instance, high structure silicic acids are obtained by effecting the precipitation at temperatures between 70° and 100° C, preferably between 80° and 85° C. It is furthermore peferable to keep the alkali number constant during the precipitation at any value between 10 and 40 and most preferably between 30 and 35. The alkali number is the titer value determined by the amount of n/10 HCl used up for 10 ml precipitation suspension at a pH up to 8.3.

The structure can furthermore be controlled by the selection of a specific $SiO_2$ end concentration. Silicic acids of high structure are obtained if the $SiO_2$ concentration is above 65 g $SiO_2$ and preferably it should be between 80 and 100 g $SiO_2$/l. A further increase of the $SiO_2$ end concentration would lead to difficulties during the mechanical dispersing action because of the increasing viscosity of the $SiO_2$ suspension.

Another feature of the invention is the use for the precipitation of acetic acid, preferably concentrated or glacial acetic acid instead of the conventionally used sulfuric acid.

Particularly good results have been obtained by successively using acetic acid and sulfuric acid as precipitation agents.

However, all of the last-mentioned structure increase due to precipitation conditions are effective only if they are employed in combination with the previously discussed mechanical dispersing conditions. What is obtained by the invention thus is a true synergistic effect.

The process of the invention apart from the obtaining of a very fine dispersion and a very high structure has still another advantage over the prior-art processes, namely, because of the precipitation in a single precipitation tank, a simplification of the entire precipitation apparatus is possible and the requirement of an adjustment of the volume of the smaller precipitation tank to the total volume of the reaction solution as it existed in the prior art processes is eliminated.

The process of the invention requires however a certain throughput frequency in the circulation through the dispersing device of the total reaction mass which must occur within a specific comparatively short time period or interval of the total reaction time and, more specifically, should occur during the flocculation or gelation phase. It is this feature which permits a reduction of the comparatively high energy requirement of the prior-art process and thus makes the process of the invention highly economical.

The process of the invention results in silicic acids which are superior in structure and fine dispersion over the prior-art products if the specific precipitation conditions such as temperature, alkali number, $SiO_2$ end concentration and type of acid are observed in combination with the optimum dispersion conditions such as timing and duration of the dispersion period and throughput frequency.

The process of the invention furthermore has the following advantage over the prior-art processes. The use of rotary pumps or corresponding dispersion devices permits to make silicic acids with a low amount of energy which, although they have a high degree of structure, have a secondary particle distribution curve of a different nature (larger size of grain size of highest incidence) than the corresponding curve of silicic acids made with regular dispersing devices (smaller size of grain of highest incidence). This is a property which is particularly of importance for certain uses of the dispersed precipitated silicic acids such as matting agents in lacquers. In the first case, that is with rotary pumps, there are obtained high structure silicic acids which have a larger secondary particle size than in the second case (ordinary dispersing device).

The development of the grain size distribution of the products of the invention accordingly can be controlled by the choice between a through-flow dispersing device, on the one hand, and a rotary pump, on the other, in spite of the presence of an equally high structure in either case.

the silicic acids made by the process of the invention have an increased fine dispersion and structure both as compared with aerogel and with spray-dried silicic acids. They are even superior to the well-known fine dispersion of silicic acids that are ground by a steam jet or air jet process.

The following table shows numerical values of a few silicic acid types and substantiates the preceding statements. All measurements were carried out with a Brabender plastograph and a Cabot kneader. The oil was added into the kneading space that was covered with a lid by means of an automatic piston buret at a constant flow speed of 2 ml/min. The absorption liquid (oil) was a technical grade dibutyl phthalate (DBP, molecular weight 278; specific weight 1.046 g/cm³; boiling point 340° C). The initial amounts of silicic acids ranged between 8 and 16 g, depending on the pore weight. In selecting the initial amount it is necessary to have the kneader volume filled sufficiently with the mass. The speed of rotation of the dynamometer was 125 rpm. All measurements were carried out at 20° C. Upon passing of the predetermined limit value of the angular momentum (usually 300 Brabender units), the flow of dibutyl phthalate from the buret was stopped automatically and the volume required was then read directly from the scale on the buret in tenths of a millimeter.

| Type of Silicic Acid | DBP-Absorption number (ml/g)* | Fraction under 2 µ grain size (wt. %)** |
|---|---|---|
| Conventional aerogel | 3.04 | 36 % |
| Conventional spray-dried silicic acid, rod mill ground (Type 1) | 2.82 | 18 % |
| Commercial spray-dried silicic acid, rod mill ground (Type 2) | 2.82 | 28 % |
| Commercial xerogel, steam jet or air jet ground | 2.28 | 41 % |
| Silicic acid of the invention, dispersed by means of a circulation pump and rod mill ground | 3.10 | 57 % |
| Silicic acid of the invention, dispersed by means of a rotary pump, and rod mill ground | 3.26 | 40 % |

*determination by the Cabot method with the Brabender plastograph
**determined by the use of a centrifugal force separator for determination of particle-size distribution manufactured by BAHCO of Sweden.

The BAHCO centrifugal force separator that is referred to herein, which was used for determining the particle-size distribution of the silicic acid products of this invention, is described in an article by K. Leschonski, that was published in Arbeitsgemeinschaft fur pharmazeutische Verfahrenstechnik, vol. 12, Nos. 1–2, pages 69–71 (1966).

The excellent absorption and dispersion properties of the silicic acids of the invention which are thus superior to the prior art products is attributed to the combination of the high structure of the silicic acids and their extremely fine particle-size distribution. This makes the products of the process of the invention useful for many types of applications, particularly as matting agents, as carriers for insecticides, and pesticides, as carriers for animal feed additives, as antiblocking agents in foils, as free-running agents in powders, as agents for beer stabilization, as toothpaste ingredients, as components of aqueous and organic silicic acid suspensions, as rubber reinforcing agents and as fillers for plastic materials and as paper fillers.

For the process of the invention, a precipitation apparatus is employed which is provided with a dispersing pump in addition to the standard apparatus which is either built into the precipitation tank or which is connected with the tank for continuous operation through a separate duct. The performance of the dispersing device can be adjusted according to the total initial precipitation volume which may for instance be 100 liters.

Specifically employed was a dispersing pump having a capacity of 2000 kilograms of water per hour driven by a 3-kilowatt motor at a speed of 8000 rpm.

However, the operation of the process is not tied down to a specific type of apparatus. Thus, preferably, dispersing pumps may be combined with simple fluid pumps and the comparatively small performance of the dispersing pump may thus be increased substantially, which will permit an increase in the initial precipitation mass. The selection of a suitable dispersing device depends also on the desired distribution of the secondary particles of the shorn high structure silicic acid.

EXAMPLES

The invention will now be illustrated by way of manufacturing and application examples. In Examples 1–6 and 9–17 there is employed the precipitation process which will presently be described. These examples illustrate in which manner an optimum in structure, fineness and energy requirement can be obtained with a precipitated silicic acid that has been subjected to a mechanical treatment during its making and how this can be obtained as a function of different dispersion parameters.

Examples 7 and 8 are comparative examples in which the mechanical treatment of the invention is not employed.

Examples 18–24 show the influence of different parameters of the precipitation in regard to the structure of the final silicic acid. Examples 25–27 show preferred uses.

GENERAL PRECIPITATION PROCESS

For the purposes of the precipitation, 67.5 l of hot water and 10.48 l sodium silicate (density: 1.17 g/cm$^3$; ratio $SiO_2:Na_2O = 3.30$) were heated upon stirring to 82.5° C. Into this initial alkaline precipitation mass there were added during the following 90 minutes, upon stirring, simultaneously sodium silicate (density 1.35 g/cm$^3$; ratio $SiO_2::Na_2O = 3.30$) at a rate of 11 l/h and a 50% sulfuric acid (density 1.4 g/cm$^3$) at a rate of 1.9 l/h. The silicic acid suspension was then adjusted to a pH value of 3.5 with 55% sulfuric acid (density 1.45 g/cm$^3$). This was effected by adding acid at a rate of 2.5 l/h for 35 minutes. The total precipitation time was 125 minutes.

This general precipitation procedure was employed in all of the following examples, unless indicated otherwise. During this time limit of 125 minutes, there was effected a mechanical treatment at specific time intervals as will be set forth in the individual examples.

EX. 1–6: TIMING AND DURATION OF SHEAR ACTION

In the following examples 1–6 the timing and the duration of the shear interval is indicated and the thus-obtained products are compared with silicic acids that were not subjected to such mechanical treatments. All physical and chemical data relating to Examples 1–8 are summarized in Table I.

EXAMPLE 1

The dispersion in this case was effected as just discussed with a circulation dispersing device without an in series connected separate rotary pump. During the entire alkaline precipitation phase from the zero to the 90th precipitation minute, the total precipitation mass amounted to 100 liters and the throughput to 2000 l/h. The per-hour throughput frequency was therefore 20 h$^{-1}$.

The $SiO_2$ suspension was then subjected to filtration on a filter press with a pressure of 4 atmospheres above normal after the acidification phase. The filter cake was then washed free of salt with water. The solids content of the cake of the mechanically treated silicic acid is higher at between 18 and 20 wt.% than the contents of not-mechanically treated silicic acids, which is between 15 and 16%. The drying of the filter cake was carried out at 110°–120° C until the loss on ignition (1000° C) was about 8–10 wt.%. The soft dried SiO$_2$ granulates were then ground in a Condux rod grinder. There were obtained 8 kg of a very finely dispersed SiO$_2$ powder.

EXAMPLE 2

The silicic acid was subjected to the process as described in Example 1, only the duration of the dispersion period was modified. It extended up to the end of the acidification phase of the precipitation and therefore included the entire alkaline and acid precipitation phase from minute zero to the 123rd minute. The grinding was effected in an impact grinder with classifier for the fine material. An impact grinder with classifier contains grinder and classifier within one device. The classifier continuously moves back the coarser particles into the grinding chamber and lets pass the fine particles. The product to be treated is obtained without any loss.

EXAMPLE 3

A silicic acid was again made as described in Example 1. However, the dispersion was carried out only between the 45th and 55th precipitation minutes, that is during the flocclation phase of the silicic acid.

EXAMPLE 4

The silicic acid was again made as in Example 1, but the dispersion was effected following the flocculation of the silicic acid from the 55th up to the 90th minute of the precipitation time.

EXAMPLE 5

The making of the silicic acid was again as in Example 1, but the dispersion was effected between the 60th and 90th precipitation minute after the flocculation point.

EXAMPLE 6

The silicic acid making again followed Example 1. The dispersion time was, however, limited to the acidification phase between the 90th and 126th precipitation minute.

EXAMPLE 7

In this example, which is included for comparative purposes, the making of the silicic acid again followed the steps of Example 1, but there was no dispersing pump employed and therefore no shearing force applied.

EXAMPLE 8

In this example, which again was for comparative purposes, the process was followed as in Example 7, but the grinding of the dry SiO$_2$ granulate was effected by means of a steam jet grinder.

The significance of the timing and duration of the mechanical treatment (shear interval) in regard to structure, secondary particle distribution and energy requirements of shorn silicic acids appears from the data in the following Table I relating to Examples 1–6 and the comparison with the unshorn silicic acids of Examples 7 and 8.

TABLE I

Significance of timing and duration of shearing period on structure, secondary particle distribution and energy requirements of mechanically treated precipitated silicic acids as compared to mechanically not-treated precipitated silicic acids.

| Ex. No. | Dispersion timing during precipitation (min.) | Corresponding precipitation phase | duration of dispersion (min.) | Structure DBP-No. (ml/g SiO$_2$) | Secondary particle (Bahco) Fraction in Wt.-% $<2.14\mu$ | $<3.38\mu$ | $<6.9\mu$ | grinding apparatus | Specific dispersion energy requirement* (kWh/kg) SiO$_2$) |
|---|---|---|---|---|---|---|---|---|---|
| 1 | 0–90 | Alkaline precipitation phase | 90 | 2.84 | 60.2 | 91.8 | 99.4 | rod mill grinder | 0.56 |
| 2 | 0–123 | Alkaline + acid precipitation phase | 123 | 2.71 | 60.7 | 92.7 | 99.8 | impact grinder with fine classifier | 0.76 |
| 3 | 45–55 | from beginning of** flocculation | 10 | 2.76 | 37.7 | 67.0 | 80.0 | rod mill grinder | 0.06 |
| 4 | 55–90 | Alkaline precipitation phase after flocculation | 35 | 2.47 | 31.2 | 60.3 | 80.8 | rod mill grinder | 0.22 |
| 5 | 60–90 | Alkaline precipitation phase after flocculation | 30 | 2.48 | 25.6 | 50.1 | 68.7 | rod mill grinder | 0.19 |
| 6 | 90–126 | acidification phase | 36 | 2.08 | 11.8 | 26.2 | 44.2 | rod mill grinder | 0.22 |
| 7 | — | — | 0 | 1.98 | 15.1 | 36.1 | 69.5 | rod mill grinder | 0 |
| 8 | — | — | 0 | 2.28 | 47.0 | 91.3 | 97.8 | steam jet grinder | 0 |

*Special dispersion energy requirement E[kWh/kg SiO$_2$] = 0.00616 · t    t Δ dispersion time in minutes
**Flocculation pt. of SiO$_2$ precipitation: 40th–50th minute Table I shows the following relationships:

a. The DBP number of the shorn silicic acid is quite markedly a function of the timing of the shearing period during the precipitation. The requirement for obtaining high DBP number values (structure) is in the first place use of a sufficient shearing force in the precipitation phase in which the first-obtained metastable silica sol to a gradually flocculated silicic acid suspension. In case of the described precipitation, this transition period is usually between the 45th and 50th minute. By including this transition phase into the shearing period a substantial structure increase of 43% can be obtained over the non-shorn silicic acid. If the transition phase sol → silicic acid suspension is not included in the shear interval, no or only a minor DBP number increase of the shorn silicic acid is observed. Without any effects is the dispersion of the suspension during the acidification phase.

b. The secondary particle distribution (degree of fineness) of the shorn silicic acids is not only a function of the timing of the shearing period during the precipitation but at the same time a function of the duration of the shearing action. In order to obtain a maximum of fine distribution, it is sufficient to include the transition phase sol → silicic acid suspension into the dispersion interval and it is furthermore necessary to effect the dispersion during the entire alkaline precipitation phase (except for the sol phase), that is in case of the above precipitation process between the 30th and 90th minute of the precipitation. In case of shorn silicic acids, it is thus possible to obtain degrees of fineness for up to 60 wt.% of below 2.0 micron. Thus, the alkaline precipitated silicic acids which are subjected to a shearing action are superior in fineness even to the finest steam jet ground alkaline precipitated silicic acids and even though these have been comminuted by the conventional rod mill grinders.

c. The specific dispersion energy requirement of the silicic acid that has been subjected to a shearing force thus depends on the fact whether a silicic acid is to be made having only a high DBP number or whether it should have a high DBP number together with a high degree of fineness. In the first case the specific energy requirement with a separated dispersing pump, for instance, may only be about 0.1 kWh/kg $SiO_2$, while in the second case the energy requirement must be at least 0.4 kWh/kg $SiO_2$.

EXS. 9–17: CIRCULATION FREQUENCY AND SHEAR GRADIENT

The significance of the throughput frequency and the shear gradient for structure, secondary particle distribution and energy requirement of mechanically treated silicic acids is illustrated by the following examples 9–17. The physical-chemical data of these shorn silicic acids are collected in Table II and compared to the unshorn silicic acids of Examples 7 and 8.

The hourly throughput frequency is determined as the ratio of hourly pumping throughput of the dispersion device relative to the total precipitation volume. This parameter has been systematically modified in the following examples for three different types of apparatus or apparatus combinations, that is for a rotary pump, a side-channel pump and a flow-through device with preceding in-series connected rotary pump. The hourly throughout frequency was varied in the range of from about 10 to about 55 $h^{-1}$.

EXAMPLE 9

The precipitated silicic acid of this example was again made as described in Example 1. However, the dispersing device was a flow-through (circulation) dispersing device with a preceding in-series-connected rotary pump. The performance of the dispersing device was 1100 l/h, so that an hourly throughput frequency was accomplished of 11 $h^{-1}$.

EXAMPLE 10

The same procedure was followed as in Example 9, but with a throughput of 2000 l/h corresponding to an hourly throughput frequency of 20 $h^{-1}$.

EXAMPLE 11

Again the procedure was the same as in Example 9 but with the throughput of 2600 l/h corresponding to an hourly throughput frequency of 26 $h^{-1}$.

EXAMPLE 12

The procedure was the same as in Example 9 but with only half the initial volume, that is with a total precipitation volume of only 50 liters. At a performance of 2600 l/h an hourly throughput frequency of 52 $h^{-1}$ resulted.

EXAMPLE 13

The silicic acid was made in accordance with the steps described in Example 1. The dispersing device, however, consisted only of a rotary pump without a separate dispersing device (flow-through pump). The dispersion was carried out with a performance of 2000 l/h and a total precipitation volume of 100 liters. This corresponded to an hourly throughput frequency of 20 $h^{-1}$.

EXAMPLE 14

The general process of making the silicic acid was the same as in Example 13. The throughput of the rotary pump in this case, however, was 3000 l/h which corresponded to an hourly throughput frequency of 30 $h^{-1}$.

EXAMPLE 15

The precipitation and making of the silicic acid was effected as in Example 13. The throughput of the rotary pump was increased to 4800 l/h. The hourly throughput frequency therefore was 48 $h^{-1}$.

EXAMPLE 16

The precipitation and making of the silicic acid were carried out as in Example 1. The dispersion device comprised a side-channel pump without a separate flow-through dispersing device. The dispersion was carried out with a throughput of 1500 l/h and a total precipitation volume of 50 liters. The hourly throughput frequency was therefore 30 $h^{-1}$.

EXAMPLE 17

The making of the silicic acid followed the steps of Example 16. However, the initial volume was doubled and the hourly throughput frequency was therefore 15 $h^{-1}$.

The following Table II is a summary of the results of Examples 9–17 and together with data regarding the comparative tests of Examples 7 and 8.

TABLE II

Effect of the throughput frequency on structure, secondary particle distribution and energy requirements of mechanically treated silicic acids compared with mechanically not-treated silicic acids

| Example No. | Dispersion Device | Through-put performance (l/h) | Precipitation volume (l) | Hourly throughput frequency of total precipitation volume [h$^{-1}$] | Structure DBP-No. (ml/g SiO$_2$) | Secondary particle distribution(Bahco) fraction, wt.-% |   |   | Specific dispersion* energy requirement (kWh/kg SiO$_2$) |
|---|---|---|---|---|---|---|---|---|---|
|   |   |   |   |   |   | <2.14μ | <3.32μ | <6.9μ |   |
| 9  | dispersion device + rotary pump | 1100 | 100 | 11    | 2.66 | 49.2 | 85.3 | 99.5 | 0.86 |
| 10 | dispersion device + rotary pump | 2000 | 100 | 20    | 2.79 | 65.2 | 93.0 | 98.0 | 0.86 |
| 11 | dispersion device + rotary pump | 2600 | 100 | 26    | 2.79 | 64.7 | 94.3 | 99.4 | 0.86 |
| 12 | dispersion device + rotary pump | 2600 | 50  | 52    | 2.80 | 73.6 | 96.9 | 99.7 | 0.86 |
| 13 | rotary pump | 2000 | 100 | 20    | 2.72 | 41.3 | 85.6 | 99.1 | 0.30 |
| 14 | rotary pump | 3000 | 100 | 30    | 2.81 | 39.5 | 89.7 | 99.1 | 0.30 |
| 15 | rotary pump | 4800 | 100 | 48    | 2.74 | 38.4 | 84.5 | 99.2 | 0.30 |
| 16 | side-channel pump | 1500 | 50  | 30**  | 2.80 | 32.6 | 75.1 | 97.3 | noted |
| 17 | side-channel pump | 1500 | 100 | 15**  | 2.50 | 19.4 | 51.1 | 86.7 | not noted |
| 7  |   | 0 | 100 | 0 | 1.98 | 15.1 | 36.1 | 69.5 |   |
| 8  |   | 0 | —   | 0 | 2.28 | 47.0 | 91.3 | 97.8 | 0 |

*Specific energy requirement: dispersion device + rotary pump E = 0.00952 . t (kWh/kg SiO$_2$) t in minutes; rotary pump: E = 0.0036 . t (kWh/kg SiO$_2$) t in minutes
**dispersion timing: 40th to 90th minute; that is, a duration of only 50 minutes.

From this table, the following results appear:

(a) The DBP number (structure) of the silicic acids that have been subjected to a shearing action with a dispersing device and a rotary pump increases with increasing throughput frequency. However, at throughput frequencies of 20 h$^{-1}$ there is an upper limit value of about 2.80 ml/g. If the throughput frequency drops below values of 20 h$^{-1}$ silicic acids can still be made with DBP numbers which lie in the transition area between silicic acids that have not been subjected to a shearing force (1.98 ml/g) and the optimum value for a dispersed silicic acid (2.80 ml/g). The upper limit value of the DBP number of 2.80 ml/g is reached upon employment of rotary or side-channel pumps only at throughput frequencies of 30 h$^{-1}$. The size of the upper DBP number limit value is therefore independent of the gradient or drop of the shearing action, that is, independent of the dispersing device; but it depends on the throughput frequency. For this reason simple rotary and side channel pumps may be used as dispersing devices. The assumption therefore appears justified that, for obtaining a specific structure, a certain turbulence rather is important than a specific energy of the shearing force.

(b) The secondary particle distribution (degree of fine grain) of the silicic acids that have been subjected to shearing action is a clear function of the shearing gradient. It is furthermore a clear function of the specific dispersion energy or shearing action energy and thus of the type of apparatus employed. While on the one hand the fine dispersion of the silicic acids that have been subjected to shearing action is definitely superior to jet ground precipitated silicic acids that have not been subjected to shearing action wherever dispersing devices are employed, it appears that the use of silicic acids that have been dispersed by rotary pumps does not bring the acid entirely in the area of the secondary particle distribution of the jet ground silicic acids. Similar is the situation with the particle fineness of the silicic acids that have been subjected to shearing action with side-channel pumps.

The fine particle size of silicic acids that have been subjected to shearing just as the DBP number is a function of the throughput frequency. An upper significant limit value is quickly reached with the use of rotary pumps but is reached only gradually when using a simple flow-through dispersing device.

c. The specific dispersion energy requirement of silicic acids that have been subjected to shearing is a function of the employed dispersion apparatus and its shearing energy. The specific power requirement of high performance dispersing pumps as a rule is about 3 to 4 times above the power requirement for ordinary flow-through pumps. A very fine particle size of silicic acids subjected to shearing can only be attained at the cost of an increased power input, (that is, it is possible only with special dispersing devices) which high energy requirement would not be the case for obtaining high structure only.

The effects of different precipitation parameters on the structure size of silicic acids that have been subjected to shearing will now be illustrated by Examples 18 to 24.

EXAMPLE 18

Effect of the Precipitation Temperature 67.5 liters of hot water and 10.48 liters of sodium silicate (density 1.17 g/cm$^3$; ratio SiO$_2$:Na$_2$O = 3.30) were heated upon stirring to the desired precipitation temperature. Into this initial alkaline volume (alkali number 20) sodium silicate (density 1.35 g/cm$^3$; ratio SiO$_2$:Na$_2$O = 3.30) was then added at a rate of 11 l/h together with 55% sulfuric acid (density 1.45 g/cm$^3$) at a rate of 1.9 l/h. The addition was made upon stirring during the 90 minutes following the initial heating. During the period between the 30th and 91st precipitation minutes, the contents of the tank amounting about 100 liters were passed, by means of a rotary pump, to a continuously operating dispersing device having a throughput of 4,700 l/h (throughput frequency 47 h$^{-1}$). The SiO$_2$ suspension was then adjusted after the 90th precipitation minute to a pH value of 3.5 by adding 55%-concentration sulfuric acid (density 1.45 g/cm$^3$)

within a period of 35 minutes at a flow rate of 2.5 l $H_2SO_4$/h. The thus-resulting $SiO_2$ end concentration is at about 80 g $SiO_2$/l. The further treatment of the suspension is effected as described in Example 1. There are thus obtained 8 kg each of an $SiO_2$ powder of which the structure properties are dependent upon the precipitation temperature as shown in the following table:

TABLE III

| Precipitation Temperature (° C) | DBP-number (Structure) (ml/g) |
|---|---|
| 75 | 2.63 |
| 85 | 2.89 |
| 95 | 2.62 |

As the results of Example 18 show, the DBP number passes through a maximum of 85° C in the range between 75 and 95° C as a function of the precipitation temperature. The preferred precipitation temperature should be therefore between about 80° and 85° C.

EXAMPLE 19

Effect of the Alkali Number:

The alkali number that is provided during the precipitation has an effect on the structure properties of a precipitated silicic acid that has been subjected to a shearing action. The alkali number is a titer value which is established as follows: 10 ml of the initial alkaline mass which is formed of water and sodium silicate (density 1.35 g/cm$^3$; ratio $SiO_2:Na_2O = 3.30$) are diluted with water so as to obtain 100 ml. The mixture is then titrated by means of a glass electrode and n/10 HCl solution so as to obtain a pH of 8.3. The number of milliliters of n/10 HCl used up determines the titer value or alkali number.

For the purpose of Example 19, there was first formed an alkaline mass having a temperature of 85° C by mixing under stirring hot water and sodium silicate (density 1.35 g/cm$^3$; ratio $SiO_2O = 3.30$) in order to obtain the desired alkali number. This alkaline initial mass was then mixed upon stirring with sodium silicate ($d = 1.35$ g/cm$^3$; ratio: 3.30) introduced at a rate of 11 l/h and 55% concentration sulfuric acid (density 1.45 g/cm$^3$) introduced at a rate of 1.9 l/h. These additions were made in each case until an $SiO_2$ end concentration of about 80 g/l was obtained.

The dispersion conditions were the same as in Example 18. However, the time of dispersion extended in each case from the beginning of the precipitation up to the completion of the alkaline precipitation phase. The acidification was carried out up to a pH of 3.5. The further treatment of the $SiO_2$ suspension was effected as in Example 18. The structure properties of the thus-obtained $SiO_2$ powder depended on the alkali number as appears from the following table:

TABLE IV

| Alkali number | Duration of precipitation (alkaline phase) = dispersion duration (in minutes) | DBP-number (Structure) (ml/g) |
|---|---|---|
| 0 | 125 | 2.40 |
| 10 | 107 | 2.87 |
| 20 | 90 | 2.89 |
| 30 | 70 | 3.10 |
| 35 | 60 | 3.04 |

TABLE IV-continued

| Alkali number | Duration of precipitation (alkaline phase) = dispersion duration (in minutes) | DBP-number (Structure) (ml/g) |
|---|---|---|
| 40 | 53 | 2.97 |

The data of Example 19 show that the DBP number of silicic acids that have been subjected to a shearing action passes through a flat maximum at an alkali number of 30 going through the range from zero to 40, and thus is a function of the alkali number. This alkali number of 30 therefore should be preferred for precipitations requiring a high DBP number.

EXAMPLE 20

Effect of the $SiO_2$ End Concentration

The $SiO_2$ end concentration obtained after precipitation also had a distinct effect on the structure properties of the silicic acids that have been subjected to shearing.

The precipitations in the tests of the present example were effected at a temperature of 85° C and an alkali number of 30. The initial alkaline mass was formed of 73 liters of water and 9.5 liters of sodium silicate (density 1.35 g/cm$^3$; ratio: 3.30). To this mass there were added as described in Example 19 simultaneously sodium silicate and dilute sulfuric acid, and in each case the addition was continued for a sufficient time to obtain after the end of the precipitation a concentration of 65 or 80 or 90 g $SiO_2$/l.

The entire precipitation mass of 100 liters was subjected to dispersion with a rotary pump having throughput of 5200 l/h (throughput frequency 52 h$^{-1}$) during the 30th precipitation minute and the end of the alkaline precipitation phase. Acidification and further treatment followed the steps described in Example 18. There were thus obtained silicic acids of which the structure was affected by the $SiO_2$ end concentration as appears from the following table:

TABLE V

| $SiO_2$ end concentration (g $SiO_2$/l) | Duration of precipitation (in minutes) | DBP-number (ml/g) |
|---|---|---|
| ca. 65 | 45 | 2.04 |
| ca. 80 | 70 | 3.00 |
| ca. 90 | 90 | 3.10 |
| ca. 95 | 100 | 3.09 |

The tests set out in this example show that the DBP number of silicic acids that are subjected to shearing at first increases steeply as a function of the $SiO_2$ end concentration and reaches an upper limit value at a $SiO_2$ concentration of between about 80 and 90 g $SiO_2$/l.

EXS. 21–24: EFFECTS OF THE TYPE OF ACID EMPLOYED

EXAMPLE 21

A silicic acid was made as in Example 20 with a precipitation duration (alkaline phase) of 70 minutes corresponding to an $SiO_2$ end concentration of 80 $SiO_2$/l.

EXAMPLE 22

The silicic acid was made as described in Example 20. The time of the precipitation was 70 minutes. Instead of the 55% $H_2SO_4$ there was however used concentrated acetic acid (density 1.049 g/cm³). The acetic acid was added up to the 70th minute at a rate of 1.84 l/h. At the same time sodium silicate was passed into the suspension of $SiO_2$ at a rate of 11 l/h. The dispersion conditions otherwise were the same as in Example 20.

The acidification of the $SiO_2$ suspension to a pH of 6.5 was effected between the 70th and 120th minute. During this latter period concentrated acetic acid (density 1.049 g/cm³) was added at a speed of 2.28 l/h.

EXAMPLE 23

It may be desirable for reasons of economy to replace part of the concentrated acetic acid by the cheaper sulfuric acid without effecting a change in the structure properties. Thus, the silicic acid was first formed as described in Example 2 up to the end of the alkaline precipitation phase. However, the acidification was effected with a 55% sulfuric acid and at a flow rate of 2.5 l/h beginning with the 70th minute and up to the 115th minute. The pH value of the $SiO_2$ suspension after the acidification was 6.5.

EXAMPLE 24

In this example, a further reduction of the amount of the expensive acetic acid was effected. The concentrated acetic acid was employed up to the 45th precipitation minute following the steps described in Example 22. From the 45th minute and up to the 70th precipitation minute 55% sulfuric acid was added instead of the concentrated acetic acid at a rate of 1.9 l/h. The acidification of the $SiO_2$ suspension to a pH of 5.2 was likewise effected by means of a 55% sulfuric acid at a rate of 2.5 l/h which step extended up to the 120th precipitation minute. The following table illustrates the interrelation between the use of concentrated acetic acid and the structure of the precipitated silicic acid which has been subjected to shearing.

TABLE VI

| Example No. | type of acid or acid combination | timing of acid addition (in min.) | DBP-number (ml/g) |
|---|---|---|---|
| 21 | 55% $H_2SO_4$ | 0 –115th | 3.00 |
| 22 | concentrated acetic acid | 0 –115th | 3.26 |
| 23 | concentrated acetic acid 55% $H_2SO_4$ | 0 –70th 70th–120th | 3.23 |
| 24 | concentrated acetic acid 55% $H_2SO_4$ | 0 –45th 45th–120th | 3.20 |

The results listed in the table show that the controlled employment of acetic acid in combination with sulfuric acid still results in a distinct structure increase of the silicic acid that has been subjected to shearing.

UTILITY

The silicic acids made by the process of the invention are particularly useful as carrier materials for pesticides, as food additives and as matting agents for lacquers.

The silicic acids made by the process of the invention are distinguished by the high absorption properties (high oil absorption) and fine particle size (good floating properties). They are therefore particularly useful as carriers and fillers for liquid, pasty and wax-like active ingredients of all kinds including also animal feed additives.

The silicic acids made by the process of the invention are further distinguished by the high value of the DBP absorption (high structure) and are superior in that respect to spray-dried silicic acids. They also have a high degree of fine grain size which is superior to the spray-dried and even to the jet-stream, that is vapor jet and air jet, ground silicic acids. As a result, the silicic acids subjected to shearing have a high absorptive power for active ingredients and an enormously high floating property in water which is not comparable to any other silicic acids. The following table will substantiate the statements just made.

TABLE VII

| Properties | Commercial silicic acid ground | Commercial silicic acid, steam jet ground | Spray-dried silicic acid, rod-mill ground | Silicic acid of the invention, rod-mill ground |
|---|---|---|---|---|
| DBP number* (ml/g) | 1.77 | 2.28 | 2.83 | 3.10 |
| oil absorption (wt.-%) | 180 | 245 | 260 | 295 |
| fraction below 2 $\mu$** (wt.-%) | 7 | 41 | 18 | 57 |
| floating properties in water (%) | 43 | 82 | 57.5 | 98.4 |
| Bet-surface (m²/g) | 230 | 230 | 180 | 246 |
| pH value | 6.5 | 6.5 | 6.6 | 6.2 |
| bulk density (g/l) | 100 | 47 | 87 | 78 |

*determination by the Cabot method with the Brabender plastograph
**determined by use of the BAHCO centrifugal force separator that was referred to hereinbefore.

The following examples show the use of the silicic acids of the invention as carriers in pesticide and animal feed compositions.

EXAMPLE 25

A silicic acid was made and subjected to a shearing action as described in Examples 1 and 22. This silicic acid was then used as carrier material and compared with other silicic acids, more specifically with a ground commercial silicic acid, with a stream jet ground commercial silicic acid and with a ground spray dried silicic acid.

In a test there was determined the amount of the malathion insecticide absorption in per cent, corresponding to the tests for oil absorption. Malathion is used as a 95% technical grade product for pesticide formulations. It is an addition product of dimethyl-dithiophosphoric acid and diethyl mercaptosuccinate. The values showing the malathion absorption are the following:

| | |
|---|---|
| Commercial silicic acid, ground | 210 % |
| Commercial silicic acid, steam-jet ground | 230 % |
| Spray-dried silicic acid, ground | 318 % |
| Dispersed silicic acid according to Example 1, ground | 316 % |
| Dispersed silicic acid, ground according to Example 22 | 351 % |

In order to determine the petroleum absorption, 5 g of the filler was triturated with a glass rod with petroleum (petroleum for chromatography, $d = 0.79$) in a 250 ml beaker. The petroleum was added dropwise from a buret. The end of the oil absorption was reached as soon as the fillerpetroleum mixture separated in the form of cakes from the glass wall when subjected to vigorous trituration and could be kneaded into a wax-like mass.

It was found that the dispersed silicic acid of Example 22 was superior in malathion absorption to the spray-dried silicic acid. The silicic acid subjected to shearing was superior to normal and also to vapor jet ground silicic acids in their absorption capabilities regarding malathion. From this it can be concluded that the dispersed silicic acids of the invention can be processed into powdery dust concentrates in which the concentration of effective ingredient can be increased to above 70 wt.-%.

Similar high concentrates can be formed also for other important pesticides such as the liquid pesticides parathion and chlordane.

Because of the high absorptive properties of the silicic acid used as carrier it is possible to lower the amount of silicic acid and to increase the amount of inexpensive mineral fillers such as kaolin in the malatione spray powders.

EXAMPLE 26

This example illustrates the very high absorptive properties of the dispersed silicic acids of the Examples 1 and 22 and their use as carriers for animal feed additives. The effective agent absorbed in this case was a 70% aqueous solution of choline chloride (density 1.21 $g/cm^3$).

In a common household mixer there were mixed 30 g of the dispersed silicic acid formed in accordance with Example 1 and 43.4 ml of a 70% choline chloride solution. The absorbed amount of choline chloride was 55 wt.%. The mixture of carrier silicic acid and active ingredient formed a loose free-flowing powder.

In a similar manner it is possible to mix the silicic acid subjected to shearing in accordance with Example 22 in an amount of 30 g with 48.2 ml of 70% choline chloride solution and to form a loose free-flowing powder. The absorbed choline chloride amount in this case was 58 wt.-%.

LACQUER COMPOSITIONS

The requirements for carrier materials regarding high structure and fine dispersion apply equally also to silicic acids that are used as matting agents.

TABLE VII

| Properties | Commercial silicic acid ground | Commercial silicic acid, steam jet ground | Spray-dried silicic acid, rod-mill ground | Silicic acid of the invention, rod-mill ground |
|---|---|---|---|---|
| DBP number* (ml/g) | 1.77 | 2.28 | 2.83 | 3.10 |
| oil absorption (wt.-%) | 180 | 245 | 260 | 295 |
| fraction below 2 $\mu$** (wt.-%) | 7 | 41 | 18 | 57 |
| floating properties in water (%) | 43 | 82 | 57.5 | 98.4 |
| Bet-surface ($m^2/g$) | 230 | 230 | 180 | 246 |
| pH value | 6.5 | 6.5 | 6.6 | 6.2 |
| bulk density (g/l) | 100 | 47 | 87 | 78 |

*determination by the Cabot method with the Brabender plastograph
**determined by use of the BAHCO centrifugal force separator that was referred to hereinbefore.

The following examples show the use of the silicic acids of the invention as carriers in pesticide and animal feed compositions.

A good matting or delustering agent must have the following properties regarding matting, thickening, fine grain dispersion and size, ease of incorporation in the lacquer.

The most important property of a silicic acid used as matting agent is its matting property, that is, its ability to reduce the gloss of lacquer films. This property is dependent in the first place on the total amount (pigment volume concentration) of silicic acid incorporated in the lacquer. The absolute amount of silicic acid, however, is limited upwards since too high a silicic acid concentration would have an unfavorable effect on certain properties of the lacquer film, such as transparency, extensibility of the film and adhesion. With an increased matting effect of the silicic acid, it is possible to get along with lower amounts of acid in order to obtain the same degree of matting, for instance a silky gloss. This advantage therefore is not only economical but has also true significance for the properties of the matted lacquer film.

The matting properties of silicic acids depend on a number of factors, that is on the silicic acid type, on the grain dispersion and grain form of the secondary particles, on the lacquer system and on the index of refraction of the silicic acid. Of particular importance is the type of silicic acid, the grain distribution in the secondary particles and the lacquer system. It can be assumed that the ideal silicic acid for matting purposes should have a grain distribution of the secondary particles between 2 and 6 $\mu$ (see L.O. Young, Paint and Varnish Production, 1952 (June) 17–20/44; L.O. Young, D.P. Barrett, Official Digest (8)8–19 (1956). Approximation to this grain range can be attained for technological reasons only with a specific grind-classifier combination and specific types of silicic acid.

However, until now it was uncertain which property of the silicic acid determined the extent of the matting capability. It has now been found that there is a close connection between the structure of the silicic acid which is measured by the dibutyl-phthalate absorption (DBP number) and the matting effect in cases where the range of the grain sizes of the compared silicic acids is more-or-less identical.

Figure 2:
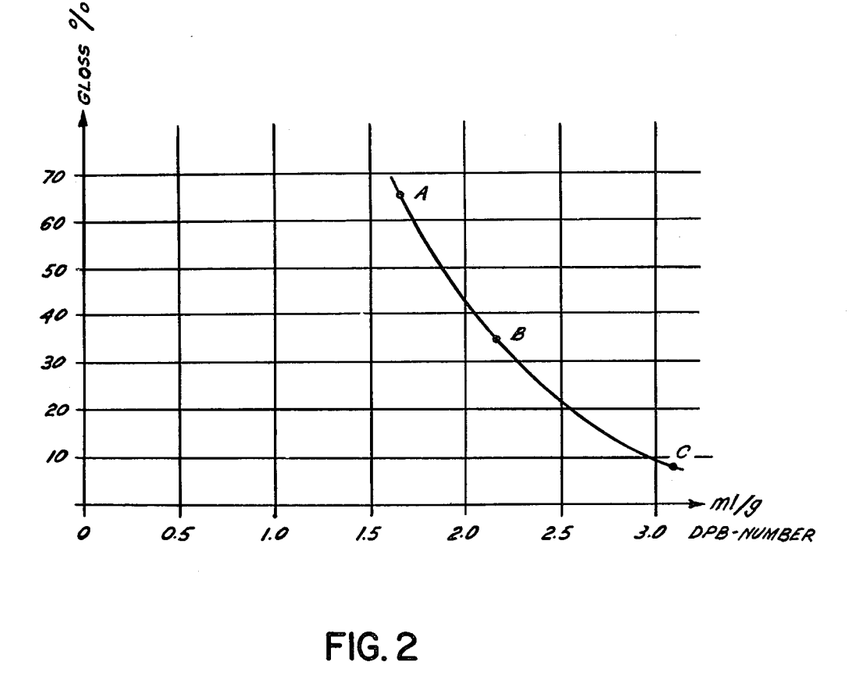
FIG. 2 is a diagram where the degree of gloss is plotted against the DBP number of three different types of silicic acid.

FIG. 2 illustrates the connection between DBP absorption and degree of gloss.

To determine the degree of gloss, which is a measurement also for the matting power of the silicic acid, the gloss-meter of B. Lange was employed. The Lange glossmeter provides an angle of incidence and reflection of 45°. The measured degrees of gloss are expressed in percentages of a standard which is set at 100%. The smaller the value of gloss turns out to be, the better is the matting power of the silicic acid. FIG. 2 shows the interrelation of the degree of gloss of a polyester resin for three different types of silicic acid: A, B and C and plots these effects as functions of the DBP number. The three types of silicic acid had the same grain spectrum but were distinguished as follows:

Silicic acid A: Wax coated commercial silicic acid of the xerogel type +)

Silicic acid B: commercial, ordinarily dried silicic acid

Silicic acid C: aerogel.

Silicic acid for delustering purposes (market name "Syloid 161") surface-modified with 15% of wax.

The aerogel has the highest DBP number and shows also the highest matting power. In summary, it can be said that in a first approximation the matting power of a silicic acid will be so much better as its structure is higher, i.e., as its DBP number is higher, and as its fraction in the 2 to 6 $\mu$ grain size is larger.

The silicic acids that are used as matting agents should impart to the lacquers if possible no or only a small thickening effect. If the thickening effect is kept within certain limits an advantageous effect will be noticed regarding the smooth flowing of the matted lacquer when sprayed. The thickening of a lacquer by the silicic acid can be measured quite accurately by a measurement of the viscosity. The viscosity is determined by means of a DIN pour beaker with a 4 mm nozzle and is stated in seconds of flow time.+). A precondition for this type of measurement is that the thickening does not take place on the basis of thixotropy. It is a serious shortcoming of the aerogels that without exception they have a thickening effect by thixotrophy on most lacquer systems which is quite pronounced and often very harmful. +) According to DIN-Normblatt Nr. 53 211. The DIN pour beaker is a measuring device for determination of the viscosity of non-thixotropic mediums.

A very find secondary particle size of the silicic acid, although causing a lower matting effect, results in a high quality of the lacquer surface. The quality of the lacquer film surface is in addition strongly affected by the dispersibility of the silicic acid. An intimate penetration of silicic acid and binder is desirable and requires a very fine particle size and a high structure in the silicic acid.

The silicic acids of the invention are superior to the aerogels by their extremely high fine particle size which is not even paralleled by the well-known fine particle size of vapor jet or air jet ground silicic acids. The silicic acids of the invention are also superior to the aerogel in the size of the structure.

Table VIII lists a number of numerical values regarding different silicic acids which will substantiate the foregoing statements.

TABLE VIII

| Type of silicic acid | DBP-number* (ml/g) | Fraction under 2 $\mu$ grain size (wt.-%)** |
| --- | --- | --- |
| commercial aerogel | 3.04 | 36 % |
| commercial silicic acid, vapor jet or air jet ground | 2.28 | 41 % |
| dispersed silicic acid of the invention, ground with a fine classifier impact grinder | 3.11 | 56 % |

*determination by the Cabot method with the Brabender plastograph
**determined by use of the BAHCO centrifugal force separator that was referred to hereinbefore.

The degree of gloss of the lacquer films which have been matted by an agent formed in accordance with the invention is considerably lower than for conventional lacquers with usual matting agents. The use of the amorphous matting silicic acid furthermore does not result in any mentionable thickening of the lacquer in spite of its very fine particle size. The thickening action is far below that of aerogels and is more or less similar to that of conventional matting silicic acids.

A further substantial advantage is in the fact that with the silicic acids of the invention a high degree of fineness of the lacquer film surface (low grindometer values) can be attained which is distinctly better than in case of use of conventional types of silicic acid.

Because of their high structure and the DBP number in connection with the high degree of dispersion of the secondary particles, the silicic acids of the invention, when used as matting agents for lacquers have a high degree of dispersibility in the sense of a genuine penetration and wetting of the silicic acid by the lacquer and the binder. The excellent dispersibility of the fine grain size silicic acid results in very good qualities of the lacquer surface which cannot be accomplished when using aerogels or precipitated silicic acids which have been formed by simple stirring.

It is furthermore surprising how rapid and simple the incorporation of the silicic acids of the invention takes place in the lacquer. The distribution in the lacquer is effected in a very short time by means of a high speed stirrer. The silicic acids of the invention are superior in this respect to aerogels which require long dispersion and grinding times in the ball mill.

The use of silicic acids which have been subjected to shearing for matting lacquers is illustrated by the following example.

EXAMPLE 27

The lacquer testing described in this example was carried out with the following silicic acids which had been subjected to shearing:

a. A silicic acid was formed which had been subjected to shearing by a dispersing device as described in Example 23. The silicic acid was however ground on an impact mill with a fine classifier.

b. A silicic acid was made as described in Example 20 and subjected to shearing by means of a rotary pump. This silicic acid was likewise ground by an impact grinder with a fine classifier.

The two types of silicic acid were tested as matting agents in four test lacquers. The results were then compared with the figures obtained with conventional xerogels and conventional aerogels.

The data regarding the lacquer technology grain analysis and physical-chemical details are summarized in Table IX. The data of the lacquer technology includes data regarding the degree of gloss which was measured by the gloss meter of B. Lange and included the viscosity and grindometer values (only in a black lacquer).

The formulations of the test lacquers were as follows:
1. Black lacquer applied by baking:

| (1) Black lacquer applied by baking: |
| --- |
| On a three-roller device a paste was prepared by trituration of the following composition: |
| 450 wt. parts "alkydal R 64" (oil modified alkyd resin) (75% in xylene) |
| 1.8 wt. parts soy- lecithin |
| 80 wt. parts n-butanol |
| 90 wt. parts carbon black |
| 631.8 wt. parts |

| The following composition was then prepared: |
| --- |
| 413 wt. parts of above paste |
| 2540 wt. parts oil-modified alkyd resin "alkydal R 64" (75% in xylene) |
| 600 wt. parts melamine resin "Maprenal WP" (55% in n-butanol) |
| 87 wt. parts n-butanol |
| 120 wt. parts ethylene glycol |
| 400 wt. parts toluene |
| 740 wt. parts xylene |
| 100 wt. parts butyl glycolate "GB-Ester" |
| 100 wt. parts butyl acetate |
| 100 wt. parts silicone oil 01 (10% in toluene) |
| 5200 wt. parts |

This mixture was adjusted with xylene to a viscosity of 23 seconds (DIN Becher, 4 mm nozzle). 5 g of the matting agent were incorporated in 100 g of lacquer with a propeller stirrer at 2000 rpm during a time of 8 minutes and were adjusted to a 20 second spray viscosity with xylene. After spraying in layers of about 35 μ the lacquer was subjected to firing for 30 minutes at 180° C.

(2) Polyurethane lacquer

| (2) Polyurethane lacquer |
| --- |
| 300 wt. parts polyester resin "Desmophen 800" |
| 400 wt. parts polyester resin "Desmophen 1100" |
| 2 wt. parts silicone oil 01 (10 % in toluol) |
| 60 wt. parts polyvinyl acetate "Mowilith 20" (50% in ethyl acetate) |
| 6 wt. parts cellulose acetobutyrate "Cellit BP 700" |
| 200 wt. parts butyl acetate (98%) |
| 140 wt. parts methoxyethyl acetate |
| 200 wt. parts ethoxyethyl acetate |
| 592 wt. parts "Shellsol A" |
| 100 wt. parts methoxybutylacetate "Butoxyl" |
| 2000 wt. parts |

10.8 g of the matting agent was added to 100 g of the above lacquer compositions and was incorporated with a high-speed stirrer at 2000 rpm during a period of 8 minutes. To this mixture there were then added 50 g of polyisocyanate ("Desmodur L") (75% concentration in ethyl acetate) and the mixture was adjusted with a DD-thinner to a viscosity of 18 seconds. The lacquer was applied in coatings of a thickness of between 30 and 40 μ.

(3) unsaturated polyester resin lacquer

| (3) unsaturated polyester resin lacquer |
| --- |
| 1040 wt. parts unsaturated polyester resin "Roskydal 500 B" |
| 260 wt. parts unsaturated polyester resin "Roskydal 500" |
| 64 wt. parts silicone oil OL (1% in toluene) |
| 572 wt. parts monostyrene |
| 1936 wt. parts |

96.8 g of the above lacquer composition, 3.2 g of an accelerator (Co-naphthenate, 10% concentration in toluene) and 6.5 g. of a matting agent were dispersed at 2000 rpm for a period of 8 minutes. The lacquer was then adjusted with ethyl acetate to a viscosity of 20 seconds and prior to spraying there were added 10 g of cyclonox paste AP (20% concentration in ethyl acetate). The lacquer was applied by spraying in coatings of thicknesses between 80 and 100 μ.

| (4) acid hardening lacquer |
| --- |
| 760 wt. parts oil modified alkyd resin "Alkydal R 40" |
| 840 wt. parts melamine resin "Maprenal SHL" (55% in n-butanol) |
| 140 wt. parts n-butanol |
| 180 wt. parts ethanol |
| 80 wt. parts silicone oil OL (1% in toluene) |

100 g of the above lacquer composition, and 9.6 g of matting agent were mixed with a high-speed stirrer at 2000 rpm for a period of 8 minutes. To each 100 g of lacquer there were then added 10 g of a 14% HCl and the mixture was adjusted with ethanol to a viscosity of 20 seconds. The lacquer was applied in coatings of a thickness between 30 and 40 μ.

The excellent properties which are obtained in matted lacquers by the use of finely divided silicic acids of high structure will appear from the following Table IX

TABLE IX

Lacquer and grain analysis data for high structure silicic acid of invention (= HS—SiO$_2$) compared with commercial silicic acids used as matting agents.

| Type of Lacquer | Type of Silicic Acid | Lacquer Data - Viscosity (DIN-beaker, 4mm) sec. | Degree of gloss(acc. to B. Lange below 40°) % | Grindo-meter value μ | Surface | Grain analysis data of SiO$_2$ prior to processing - Grain size limit: μ | Fraction in grain range 2–6μ: wt.-% | DBP-number (Cabot-method) ml/g |
|---|---|---|---|---|---|---|---|---|
| Black Baking Lacquer | aerogel: | 43 | 5.5 | 33 | good | 8.5 | 62.7 | 2.94 |
| | xerogel: | 36 | 5.5 | 36 | good | 16.0 | 71.5 | 2.14 |
| | HS—SiO$_2$ Ex. 27a | 32 | 3.5 | 27 | very good | 7.0 | 43.6 | 3.11 |
| | Ex. 27b | 36.5 | 4.0 | 34 | good | 8.5 | 66.5 | 2.81 |
| Unsaturated Polyester resin Lacquer | aerogel: | 47 | 20.5 | — | good | — | — | — |
| | xerogel: | 24 | 33.0 | — | good | — | — | — |
| | HS—SiO$_2$ Ex. 27a | 25.5 | 19.0 | — | very good | — | — | — |
| | Ex. 27b | 26 strongly thixo-tropic* | 16.0 | — | good | — | — | — |
| Poly-ester resin Lacquer | aerogel: | strongly thixo-tropic | 19.5 | — | good | — | — | — |
| | xerogel: | 25 | 36.0 | — | good | — | — | — |
| | HS—SiO$_2$ Ex. 27a | 35 | 9.5 | — | very good | — | — | — |
| | Ex. 27b | 30 strongly thixo-tropic | 10.0 | — | good | — | — | — |
| Acid Harden-ing Lacquer | aerogel: | | 3.0 | — | good | — | — | — |
| | xerogel: | 70 | 7.0 | — | good | — | — | — |
| | HS—SiO$_2$ Ex. 27a | 80 | 3.2 | — | very good | — | — | — |
| | Ex. 27b | 62 | 4.5 | — | good | — | — | — |

*could not be measured with the PIN-beaker, 4 mm.

We claim:

1. A process for the production of a fine-grain, amorphous, high structure silicic acid comprising the steps of precipitating a silicic acid by heating an aqueous alkali-metal silicate solution to a temperature between 70° and 100° C, then adding an acid or an acidic-acting substance or a mixture of said acid and acidic-acting substance together with further alkali-metal silicate to the said heated solution, thus causing the mixture to pass first through an alkaline phase and then through an acid precipitation phase, whereby a gradual transition of the silicate to an intermediate hydrated silica sol and thereafter gradual conversion of the hydrated silica sol by flocculation to a silicic acid suspension occurs in said alkaline phase and these steps being carried out with the following provisions:
   a. the alkali number of the reaction mixture is maintained substantially constant throughout the said alkaline precipitation phase at a value within the range from 10 to 40;
   b. the amounts of components for the precipitation reaction are selected to obtain an SiO$_2$ end concentration above 65 grams SiO$_2$ per liter;
   c. a dispersing and shearing force is applied to the mixture throughout the major part of the period of said gradual conversion of the intermediate hydrated silica sol to the flocculated silicic acid;
   d. the said dispersing and shearing force is applied by passing the mixture in a continuous stream through a flow-through dispersing pump, centrifugal pump, or combination of these devices, the said pump operating at a frequency of at least 10 per hour, the said frequency being the ratio of the performance of the dispersing device expressed in cubic meters per hour to the initial volume of the reaction mixture in cubic meters; and
   e. the said mixing, precipitation and suspension formation is carried out in a single reaction vessel.

2. A process as defined in claim 1 in which the precipitation is effected in the presence of a neutral salt.

3. A process as defined in claim 1 in which the alkali number of the mixture is maintained between 30 and 35 during the alkaline precipitation phase.

4. A process as defined in claim 1 in which the amounts of the components for the precipitation mixture are selected to obtain an SiO$_2$ end concentration between 80 and 100 grams SiO$_2$ per liter.

5. A process as defined in claim 1 in which the dispersing and shearing force is applied throughout the entire period of the gradual conversion of the intermediate hydrated silica sol to the flocculated silicic acid.

6. A process as defined in claim 1 in which the pump is operated at a frequency between 20 and 100 per hour.

7. A process as defined in claim 1 in which up to 60% by weight of the silicic acid particles that are produced have a particle size below 2 microns.

8. A process as defined in claim 1 in which the acid or acidic-acting substance that is added to the heated aqueous alkali-metal silicate solution is acetic acid, ethyl acetate, sulfuric acid, or a mixture of one or more of these, or acetic acid and sulfuric acid are both used but are added separately and successively.

9. A process as defined in claim 8 in which the acid that is added to the heated aqueous alkali-metal silicate solution is concentrated acetic acid.

* * * * *

UNITED STATES PATENT OFFICE
CERTIFICATE OF CORRECTION

Patent No. 4,001,379  Dated January 4, 1977

Inventor(s) Gunter TÜRK and Joseph WELSCH

It is certified that error appears in the above-identified patent and that said Letters Patent are hereby corrected as shown below:

63] Continuation of Ser. No. 199,054, Nov. 15, 1971, abandoned, which is continuation of Ser. No. 819,739, April 28, 1969, abandoned.

Signed and Sealed this

Twenty-first Day of June 1977

[SEAL]

Attest:

RUTH C. MASON
Attesting Officer

C. MARSHALL DANN
Commissioner of Patents and Trademarks